United States Patent
Broesky (10) Patent No.: US 11,730,289 B2
(45) Date of Patent: Aug. 22, 2023

(54) HEATED BOAT BLANKET

(71) Applicant: Anne-Marie Broesky, Kelowna (CA)

(72) Inventor: Anne-Marie Broesky, Kelowna (CA)

(73) Assignee: SURFINITY, Kelowna (CA)

(*) Notice: Subject to any disclaimer, the term of this patent is extended or adjusted under 35 U.S.C. 154(b) by 64 days.

(21) Appl. No.: 17/224,097

(22) Filed: Apr. 6, 2021

(65) Prior Publication Data
US 2022/0312990 A1    Oct. 6, 2022

(51) Int. Cl.
A47G 9/02    (2006.01)
A61F 7/00    (2006.01)
A47G 9/06    (2006.01)

(52) U.S. Cl.
CPC ......... *A47G 9/0215* (2013.01); *A47G 9/0223* (2013.01); *A47G 9/066* (2013.01); *A61F 7/0097* (2013.01); *Y10S 5/941* (2013.01)

(58) Field of Classification Search
CPC .............. A47G 9/0215; A47G 9/0223; A47G 2200/16; A47G 9/066; A61F 2007/006; A61F 7/0097; H05B 3/342; H05B 1/0236; H05B 1/0072; H05B 3/0042; H05B 2203/023; Y10S 5/941; B68G 1/00
See application file for complete search history.

(56) References Cited

U.S. PATENT DOCUMENTS

2003/0191514 A1* 10/2003 Chatham ............... A61F 7/0097
607/107

FOREIGN PATENT DOCUMENTS

WO    WO-9908631 A1 *  2/1999  ............. A61B 46/00

OTHER PUBLICATIONS

"Amazon.com: Large Waterproof Boat Blanket by Mambe—Royal—Insulated . . . " Amazon, Mambe—Waterproof Blankets, May 11, 2015, https://www.amazon.com/Large-Waterproof-Boat-Blanket-Mambe/dp/B09C6R358H.*
"Mambe Boat Blanket: Waterproof Boat Blanket." Mambe Blanket Co., https://mambeblankets.com/products/boatrave?variant=3972668036.*

* cited by examiner

*Primary Examiner* — David R Hare
*Assistant Examiner* — Madison Emanski (57) ABSTRACT

The present invention relates to a heated blanket for use on a boat. The blanket has a top layer which is nylon, and a bottom layer which is fleece. There are one or more heater hose inserts (or openings) on each side and one or more foot pockets. The one or more heater hose inserts may be inserted with one or more heater hoses of a boat. The one or more heater hoses may blow in hot air. The hot air fills in the blanket, thereby warming the surrounding environment, which in turn warms the user body who is using the blanket. The blanket prevents the loss of body heat while utilizing the on-board heater hose to keep the user warm.

1 Claim, 7 Drawing Sheets

HEATED BOAT BLANKET

TECHNICAL FIELD OF THE INVENTION

The present invention relates in general to blankets, and, more particularly, to heated blankets for warming purposes. The blankets are heated using thermal heating from one or more heater hoses of a boat.

BACKGROUND OF THE INVENTION

A blanket is a piece of soft cloth large enough either to cover or to enfold a great portion of the users body, especially during cool summer nights, spring or fall days, when sleeping or otherwise at rest, thereby trapping radiant bodily heat that otherwise would be lost through convection, and so keeping the body warm. There are various types of blankets, such as bedclothes, that are used for covering the user's body in order to warm it. All these require auxiliary heating apparatus or utilize internal electrical heating elements. However, the prior art lacks efficient and effective blankets that can be used by one or more users on a boat during a boating experience in a water body such as a river or a lake. Boating is a leisurely activity of travelling by boat, or the recreational use of a boat whether powerboats, sailboats, or man-powered vessels (such as rowing and paddle boats), focused on the travel itself; as well as sports activities, such as fishing or waterskiing. Whether the user is out on a lake to relax or competing at high speeds against other boats, boating can be a great activity for the user's health and fitness. However, during the boating, there is a high chance of the users getting wet, either due to splash of water or swimming activities experienced during the boating. In each case, a user may feel cold, and thus needs dry clothes for warming. Also, while boating, especially during early morning or late evening or night time, the users body experiences cold and thus needs warmer clothes to overcome or withstand the cooling temperature. Although the use of warmer clothes has been known since ages, nowadays electric blankets are highly preferred. However, for using the electric blankets on the boat during the boating activities, the user may be required to carry the additional heating components associated with the electric blankets. Additionally, the boat should have an additional power source for powering the electric blankets. However, the user may not be comfortable carrying the electric blankets all the time, plus there is the additional requirement of having the power source for powering the electric blankets that may not be available on the boat. Also, the use of electric blankets may not be safe for the users especially while boating. During boating, a user needs a blanket that is safe and readily available without endangering the occupants of the boat.

In light of the above, there is a need in the art for an improved blanket for warming purposes, especially for use on a boat while boating or surfing in a water body such as a lake, ocean or a river. It is to these ends that the present invention has been developed.

BRIEF SUMMARY OF THE INVENTION

To minimize the limitations in the prior art, and to minimize other limitations that will be apparent upon reading and understanding the present specification, the present invention describes a heating blanket for warming the user's body while boating or after enjoying watersports in a water body such as a lake, ocean or a river. The heated boat blanket, described in the present invention, has been designed to keep the users body warm on a boat during the boating or after enjoying watersports. Also, the use of the heated boat blanket may facilitate in a great way to extend the boating hours and extend the boating season. The heated boat blanket may be very essential when the users are surfing or boating in the spring or fall or during those cold mornings and evenings.

It is an objective of the present invention to provide a heated blanket for use on a boat. The blanket has a top layer which is nylon, and a bottom layer which is fleece. There are one or more heater hose inserts (or openings) on each side and one or more foot pockets. The one or more heater hose inserts may be inserted with one or more heater hoses of a boat. The one or more heater hoses may blow in hot air. The hot air fills in the blanket, thereby warming the surrounding environment, which in turn warms the user body who is using the blanket.

It is another objective of the present invention to provide the blanket that may be fed with heat (i.e., the hot air) from one or more boat's retractable hoses or pipes that are connected to a boat's heater system.

These and other advantages and features of the present invention are described herein with specificity so as to make the present invention understandable to one of ordinary skill in the art, both with respect to how to practice the present invention and how to make the present invention.

BRIEF DESCRIPTION OF THE SEVERAL VIEWS OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

The novel features which are believed to be characteristic of the present invention, as to its structure, organization, use and method of operation, together with further objectives and advantages thereof will be better understood from the following drawings in which a presently preferred embodiment of the invention will now be illustrated by way of various examples. It is expressly understood, however, that the drawings are for the purpose of illustration and description only and are not intended as a definition of the limits of the invention. Embodiments of this invention will now be described by way of example in association with the accompanying drawings in which.

DETAILED DESCRIPTION OF THE INVENTION

Certain terminology is used in the following description for reference only and is not limiting. The words "front," "rear," "anterior," "posterior," "lateral," "medial," "upper," "lower," "outer," "inner," and "interior" refer to directions toward and away from, respectively, the geometric center of the invention, and designated parts thereof; in accordance with the present disclosure. Unless specifically set forth herein, the terms "a," "an," and "the" are not limited to one element, but instead should be read as meaning "at least one." The terminology includes the words noted above, derivatives thereof; and words of similar import.

The present invention relates in general to blankets, and, more particularly, to heated boat blankets for warming purposes. The blankets are heated using thermal heating from one or more heater hoses of a boat. The present invention describes the heating boat blanket for warming the user's body while boating or after enjoying watersports in a water body such as a lake, ocean or a river. The heated boat blanket, described in the present invention, has been designed to keep the user's boy warm on a boat during the boating or after enjoying watersports.

Before describing the present invention in detail, it should be observed that the present invention utilizes a combination of components, which constitutes the heating boat blanket for warming the user's body in a boating or surfing environment. Accordingly, the components have been represented, showing only specific details that are pertinent for an understanding of the present invention so as not to obscure the disclosure with details that may be readily apparent to those with ordinary skill in the art having the benefit of the description herein. As required, the detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

References to "one embodiment", "an embodiment", "another embodiment", "yet another embodiment", "one example", "an example", "another example", "yet another example", and so on, indicate that the embodiment(s) or example(s) so described may include a particular feature, structure, characteristic, property, element, or limitation, but that not every embodiment or example necessarily includes that particular feature, structure, characteristic, property, element, or limitation. Furthermore, repeated use of the phrase "in an embodiment" does not necessarily refer to the same embodiment.

The words "comprising", "having", "containing", and "including", and other forms thereof are intended to be equivalent in meaning and be open ended in that an item or items following any one of these words is not meant to be an exhaustive listing of such item or items or meant to be limited to only the listed item or items. While various exemplary embodiments of the disclosed blankets have been described below, it should be understood that they have been presented for purposes of example only, and not limitations. It is not exhaustive and does not limit the invention to the precise form disclosed. Modifications and variations are possible in light of the above teachings or may be acquired from practicing of the invention, without departing from the breadth or scope.

The heating boat blanket of the present invention will now be described with reference to the accompanying drawings, which should be regarded as merely illustrative without restricting the scope and ambit of the present invention.

Figure 1:
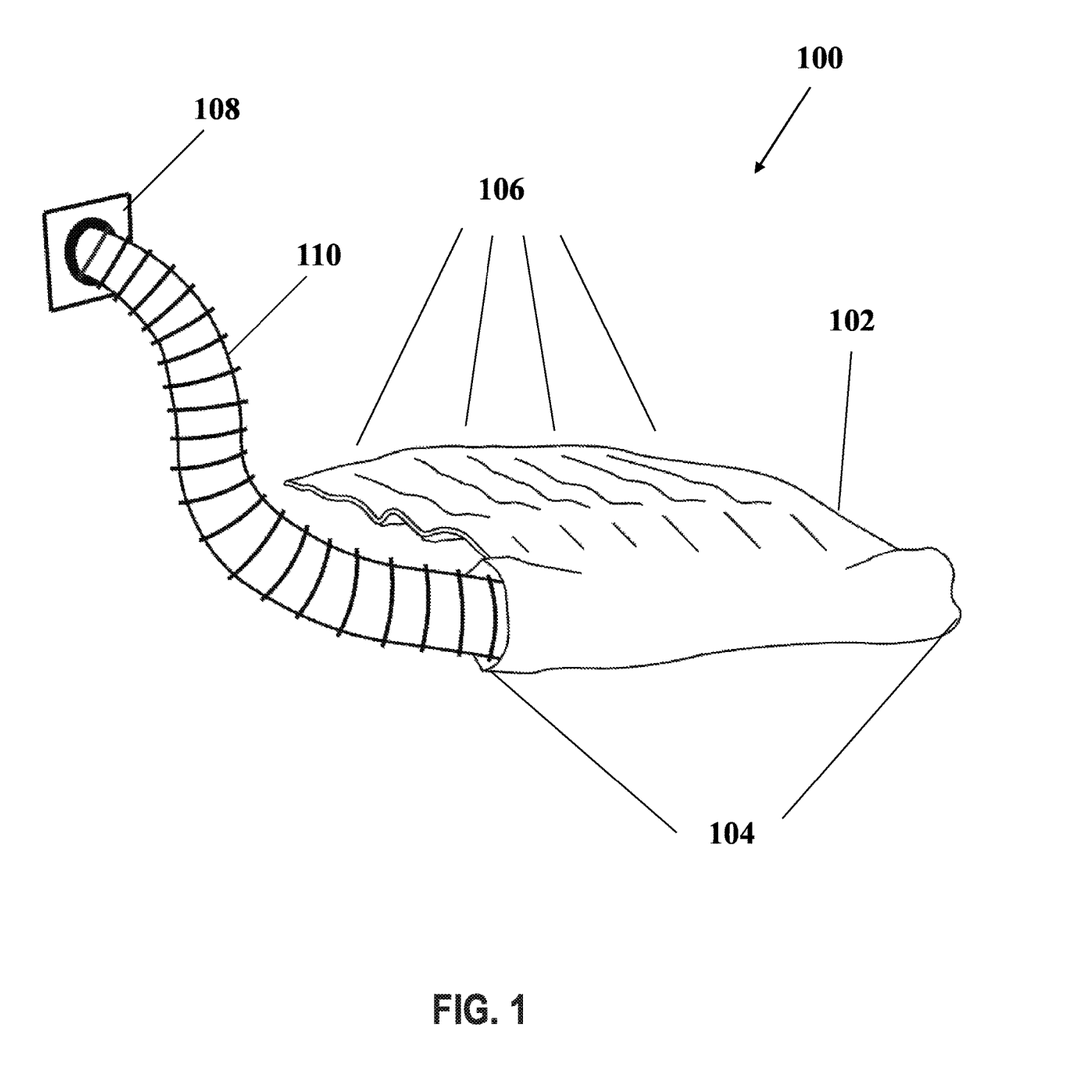
FIG. 1 illustrates a boat blanket assembly, according to an exemplary embodiment of the present invention.

FIG. 1 illustrates a boat blanket assembly 100, according to an exemplary embodiment of the present invention. The boat blanket assembly 100 illustrates a blanket 102. The blanket 102 includes one or more hose inserts or openings such as a hose insert 104. The blanket 102 further includes one or more sewn channels such as sewn channels 106. There is further shown a boat heater hose 108 of a boat. The boat heater hose 108 is removably attached or connected to a retractable heating hose or pipe 110.

The blanket 102 is a piece of cloth large enough either to cover or to enfold a great portion of a user's body, usually when sleeping or otherwise at rest, thereby trapping radiant bodily heat that otherwise would be lost through convection, and so keeping the body warm. The blanket 102 is provided with a plurality of layers such as a top layer and a bottom layer. The top layer is nylon, and the bottom layer is fleece.

In an embodiment, there are two heater hose inserts (such as the hose insert 104) on each side as shown in FIG. 1. Each hose insert 104 is used for inserting the retractable hose 110. For example, the retractable hose 110 (that is removably attached to the boat heater hose 108 of the boat for collecting hot air) is inserted into the hose insert 104. The retractable hose 110 blows in the hot air inside the hose insert 104 that is uniformly distributed inside the body of the blanket 102. In an embodiment, the sewn channels 106 allow the hot air to efficiently flow through all channels of the blanket 102. Furthermore, adding the integrated channels allow the user to handle the blanket 102 an efficient and effective manner. For example, with the old blankets in the prior art, it would blow up like a balloon and it would be hard to control these blankets from blowing around. The user had to constantly keep his hands on it when the boat is moving. However, adding the integrated channels to the blanket 102 of the present invention allows easier handling of the blanket 102 by the user.

Figure 2:
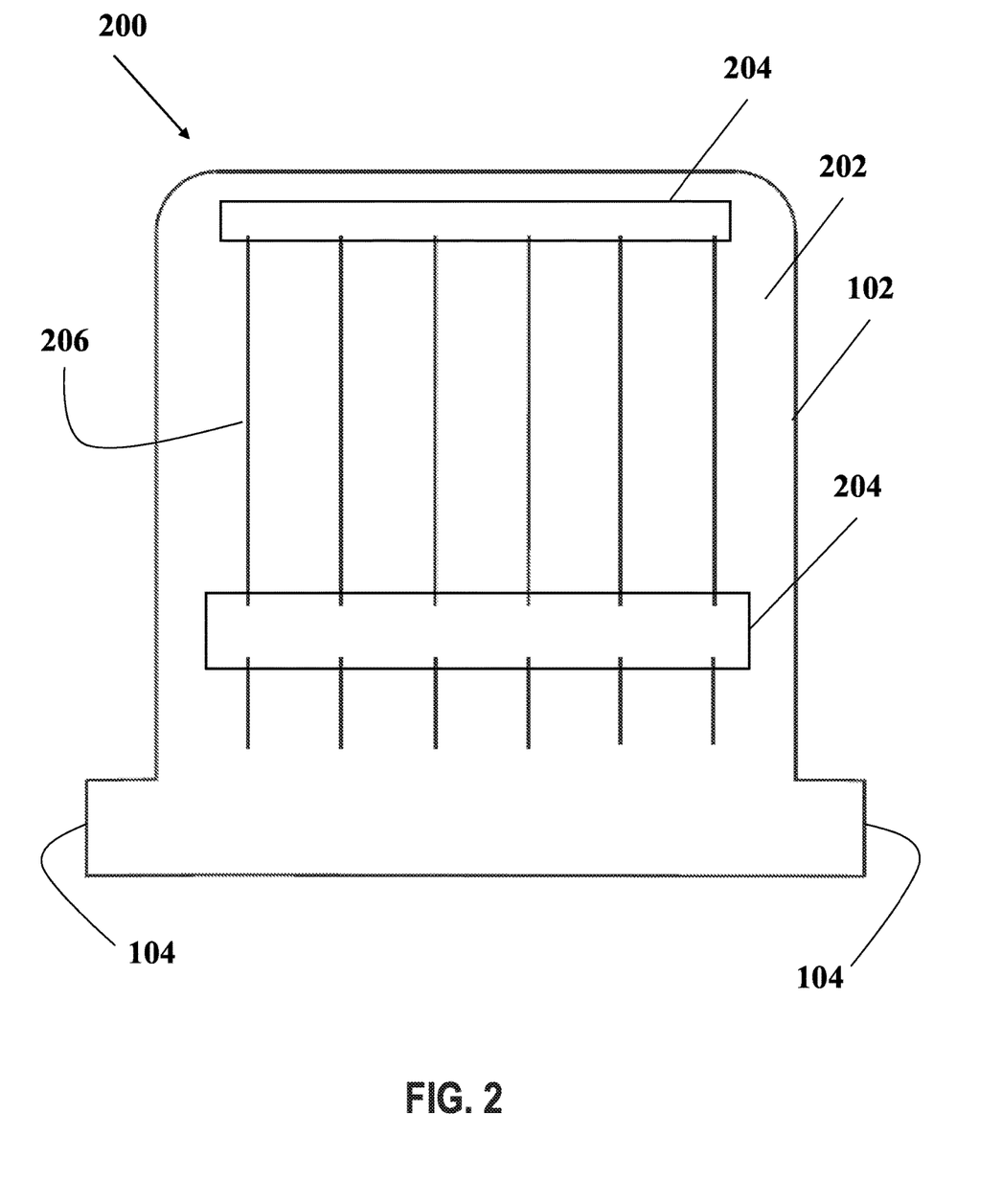
FIG. 2 illustrates a front view of the boat blanket, according to an exemplary embodiment of the present invention.

FIG. 2 illustrates a front view 200 of the boat blanket 102, according to an exemplary embodiment of the present invention. The front view 200 illustrates the top layer of the blanket 102 that is made up of a material called nylon 202. There is further shown a special sewn channel pattern 206 with one or more break points such as break points 204. In one exemplary embodiment, the one or more break points may be provided at a position that is ¾ down the blanket but not limited to 20 inches, 40 inches, 50 inches or any other distance along the length of the blanket as measured from a top edge 102. This allows the hot air to flow through all channels in an efficient and effective manner. In an embodiment, each break point 204 in the channels is a point where two layers (i.e., the top and bottom layers) of the fabrics (i.e., the nylon 202 and the fleece) are not sewn together, which in turn allows the hot air to flow through all channels in an efficient and effective manner. For the simplicity of the ongoing discussion, only one break point 204 has been shown between ends of the blanket 102. However, a person having ordinary skills in the art would understand that the blanket 102 may be provided with multiple break points (such as the break point 204) for facilitating the hot air to flow through all channels in much more efficient and effective manner.

In an embodiment, as shown in FIG. 2, the hose insert 104 is located at the bottom of the blanket 102 i.e., below the sewn channel pattern 206 of the blanket 102. Further, a horizontal width of a portion of the blanket 102 including the hose insert 104 is greater than a horizontal width of a portion of the blanket 102 including the sewn channel pattern 206 i.e., the hose insert 104 extends outward in comparison to the portion of the blanket 102 including the sewn channel pattern 206. As shown in FIG. 2, there are two hose inserts 104. In one exemplary scenario, both of the hose inserts 104 are fitted with a separate retractable heating hose 110 for blowing in the hot air. In another exemplary scenario, only one of the two hose inserts 104 is fitted with the retractable heating hose 110 for blowing in the hot air. In this scenario, the other hose insert 104 is kept close so as to disallow the hot air to escape through.

Figure 3:
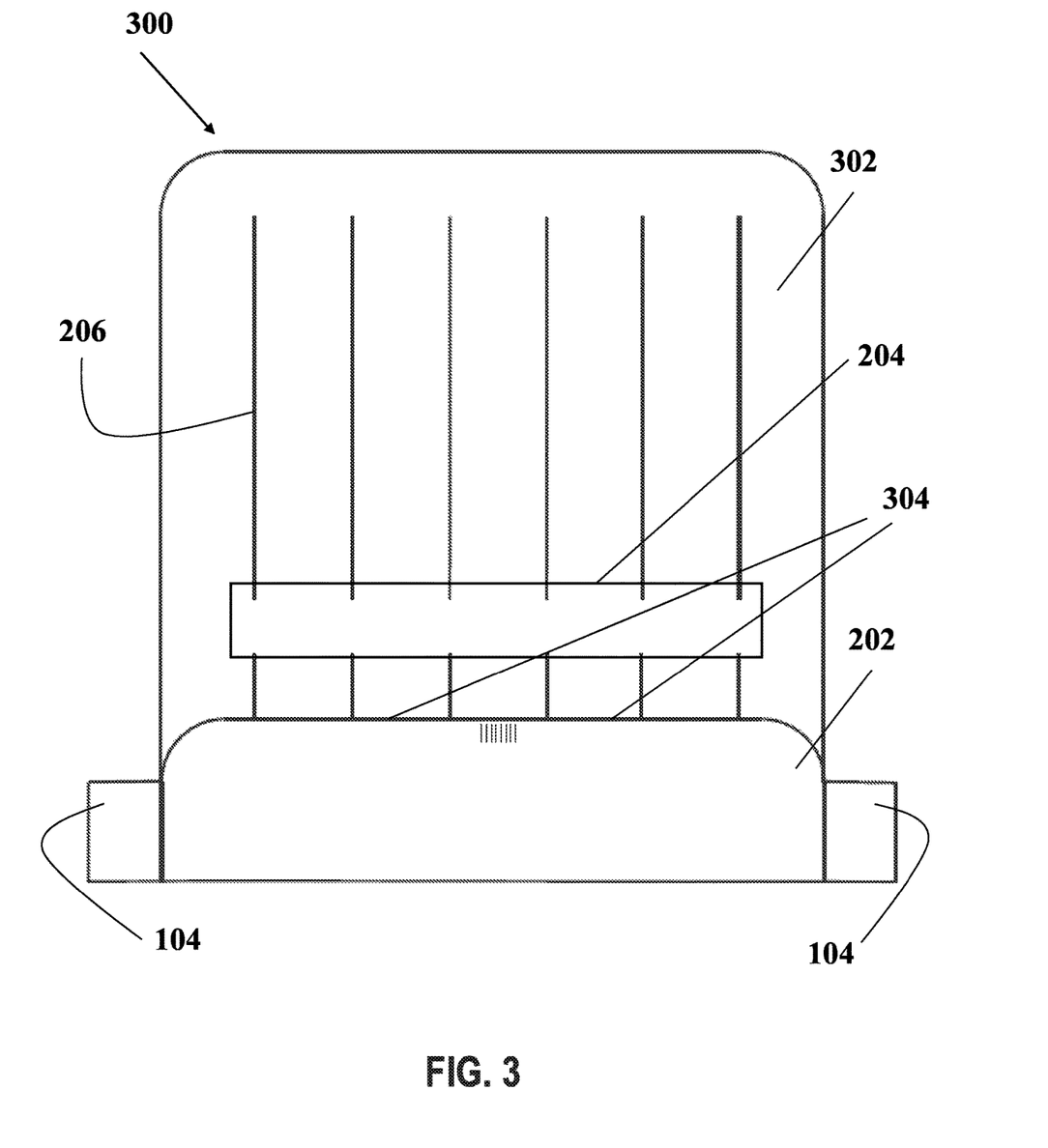
FIG. 3 illustrates a rear view of the boat blanket, according to an exemplary embodiment of the present invention.

FIG. 3 illustrates a rear view 300 of the boat blanket 102, according to an exemplary embodiment of the present invention, the rear view 300 illustrates the bottom layer of the blanket 102 that is made up of a material called fleece 302. The sewn channel pattern 206 including the one or more sewn channels may be formed by sewing the top nylon layer 202 with the bottom fleece layer 302 inside edges of the blanket 102. The top nylon layer 202 may be sewed to the bottom fleece layer 302 such that it includes the one or more break points such as the break points 204. Also, the top nylon layer 202 and the bottom fleece layer 302 may be sewn together along its edges so that the hot air does not escape the blanket 102 and keeps it warmer. The bottom layer of the blanket 102 further includes one or more pockets such as pockets 304 that is used for inserting or positioning feet of the user. Each foot may be inserted into each pocket 304 while using the heated boat blanket 102. Each foot pocket 304 is made up of a material called the nylon 202 which is an extension layer of the top nylon layer 202 towards the bottom layer through the hose inserts 104. The two feet pockets 304 may be provided such that they are separate from each other.

Figure 4:
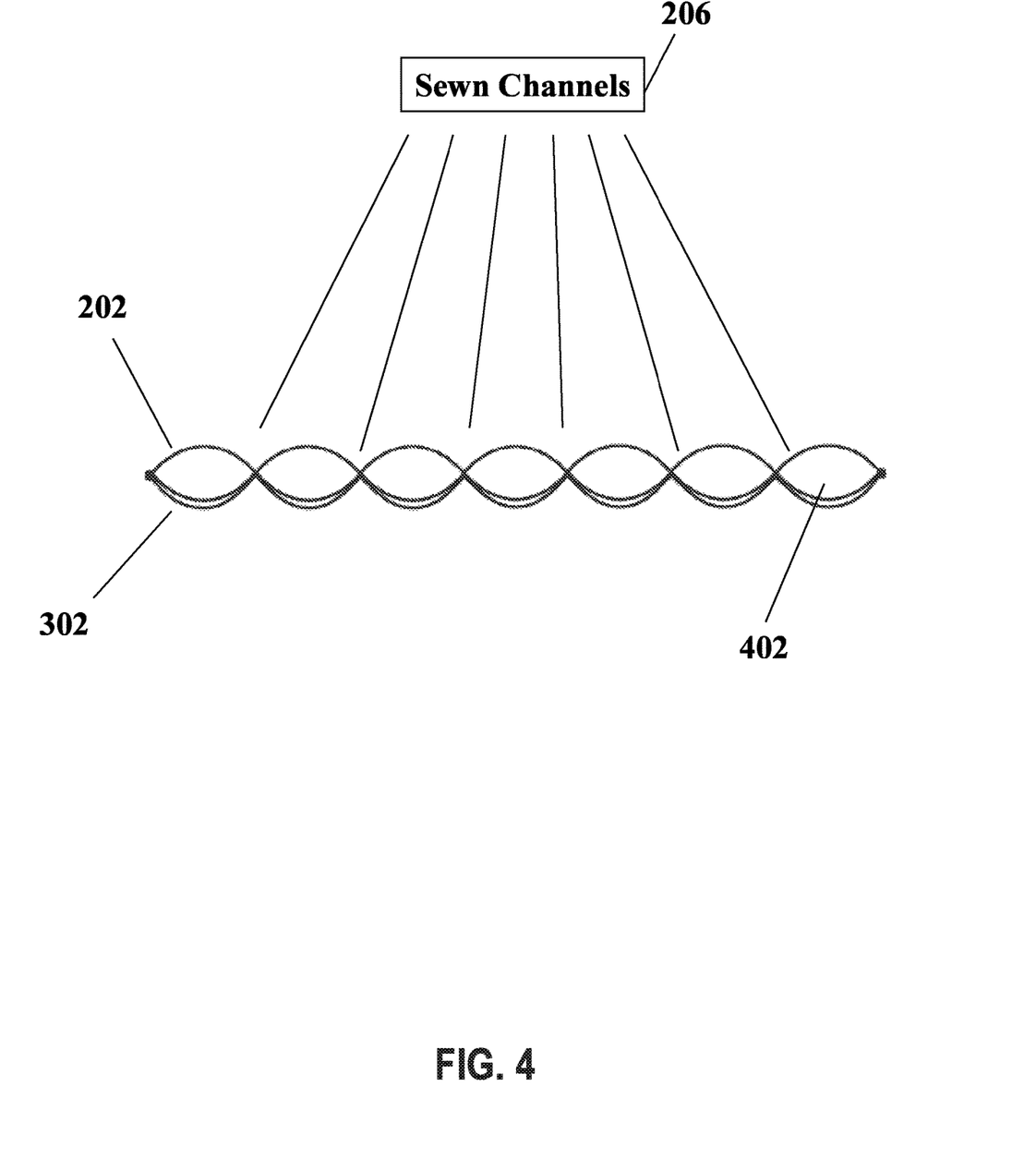
FIG. 4 illustrates sewn channels of the boat blanket, according to an exemplary embodiment of the present invention.

FIG. 4 illustrates sewn channels 206 of the boat blanket 102, according to an exemplary embodiment of the present invention. The sewn channels 206 may be formed by sewing the top nylon layer 202 with the bottom fleece layer 302. The top nylon layer 202 may be sewed to the bottom fleece layer 302 such it includes the one or more break points. One or more air channels 402 formed by the sewn channels 206 facilitate uniform flow or distribution of the hot air from the retractable hose 110 (that is removably attached to the boat heater hose 108 of the boat for collecting the hot air) inside the blanket 102 via the sewn channels 206.

Figure 5:
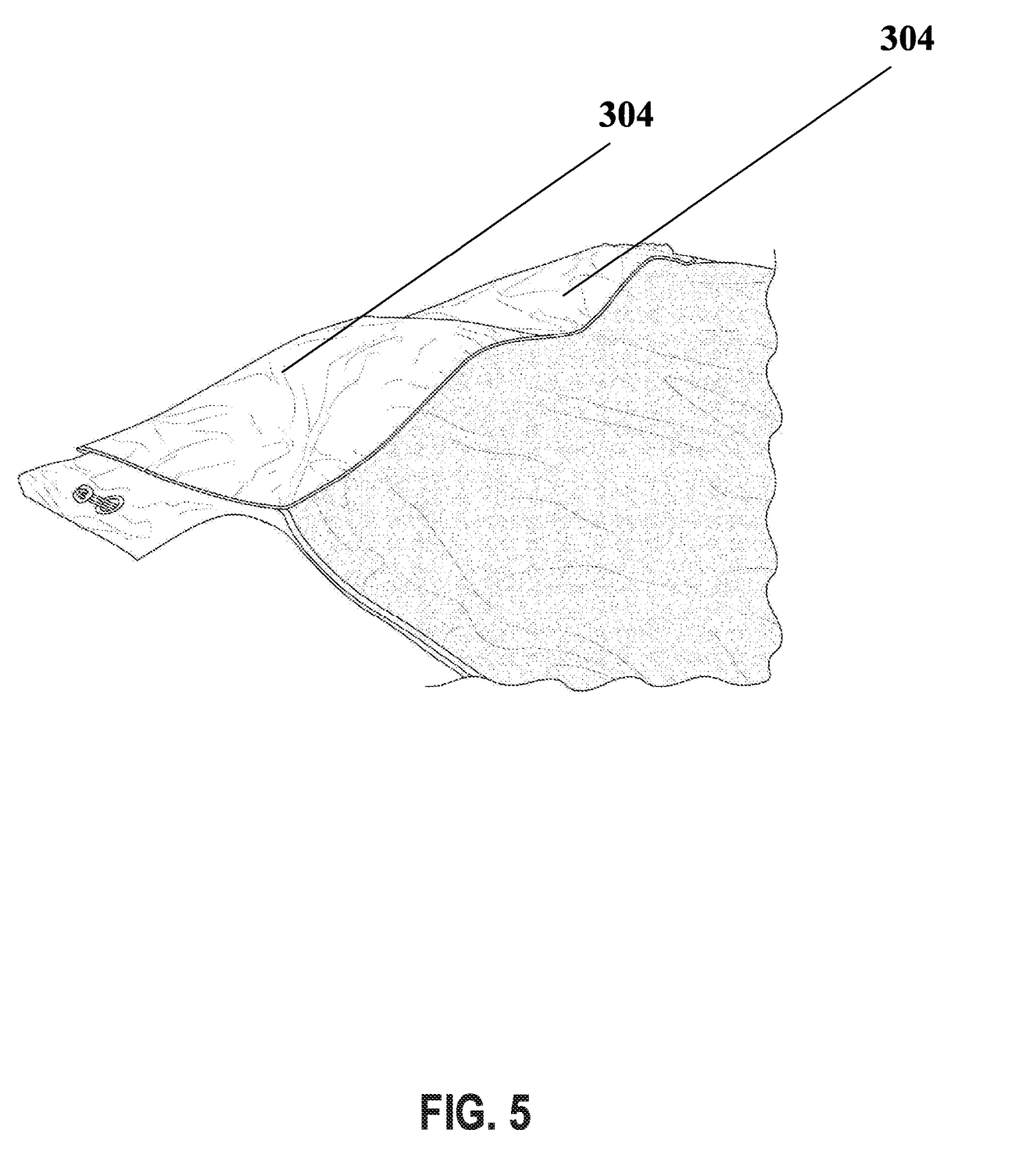
FIG. 5 illustrates feet pockets of the boat blanket, according to an exemplary embodiment of the present invention.

FIG. 5 illustrates the feet pockets 304 of the boat blanket 102, according to an exemplary embodiment of the present invention. The feet pockets 304 are actually the same two pieces sewn together. For example, if someone is looking at the front of the blanket 102, then before the last part is sewn, the blanket 102 may extend past down the hose inserts 104. The blanket's bottom is then pulled around the back and stitched about 16 inches up in the back to create the feet pockets 304.

Figure 6:
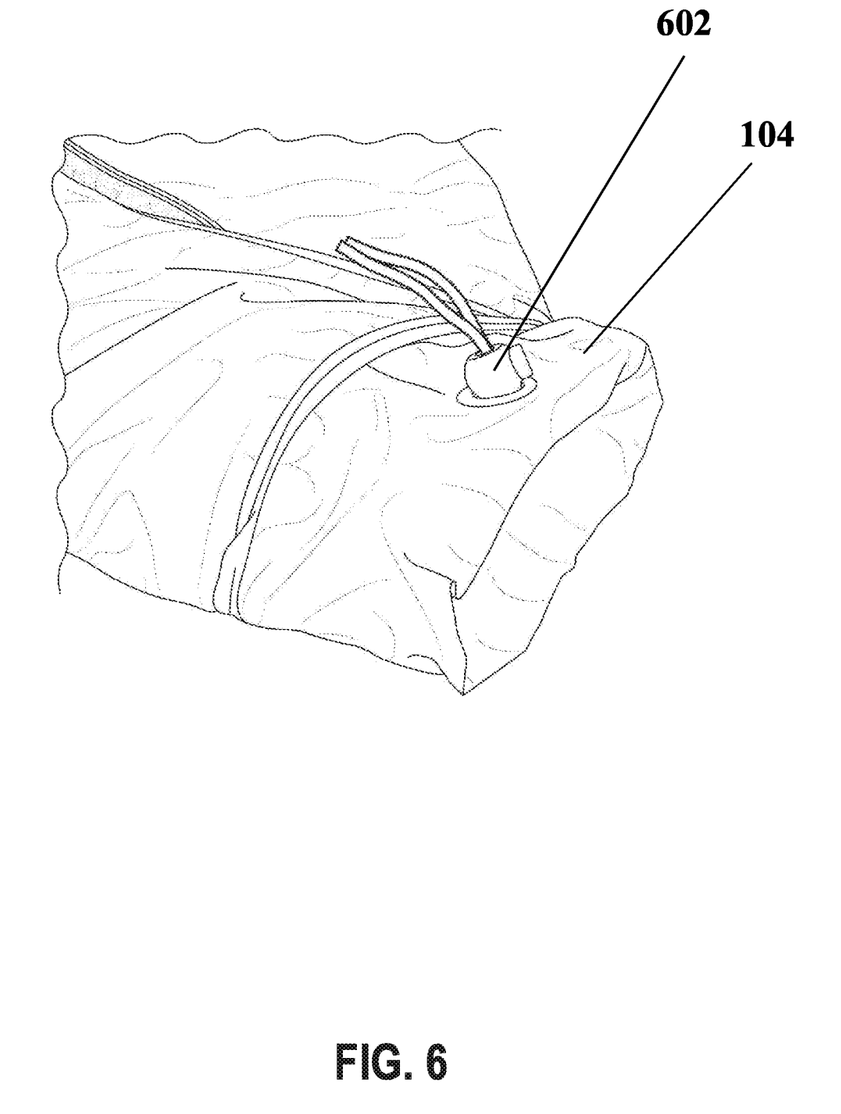
FIG. 6 illustrates a blanket hose insert or opening of the boat blanket, according to an exemplary embodiment of the present invention.

FIG. 6 illustrates the blanket hose insert 104 of the boat blanket 102, according to an exemplary embodiment of the present invention. In an embodiment, the blanket hose insert 104 may be included with a draw string closure 602. In a scenario where the retractable hose 110 is not inserted into the blanket hose insert 104, the draw string closure 602 may be used to close the opening of the blanket hose insert 104 and the blanket 102 may be used as a normal blanket. In another scenario, the draw string closure 602 may be used to tighten the hose insert 104 of the blanket 102 to the retractable hose 110. In a scenario where only one retractable hose 110 is being used for blowing in the hot air into the blanket 102, the draw string closure 602 of the other hose insert 104 may be used to close down the other retractable hose 110 so that the hot air does not escape the blanket 102 and keeps it warmer during the use.

Figure 7:
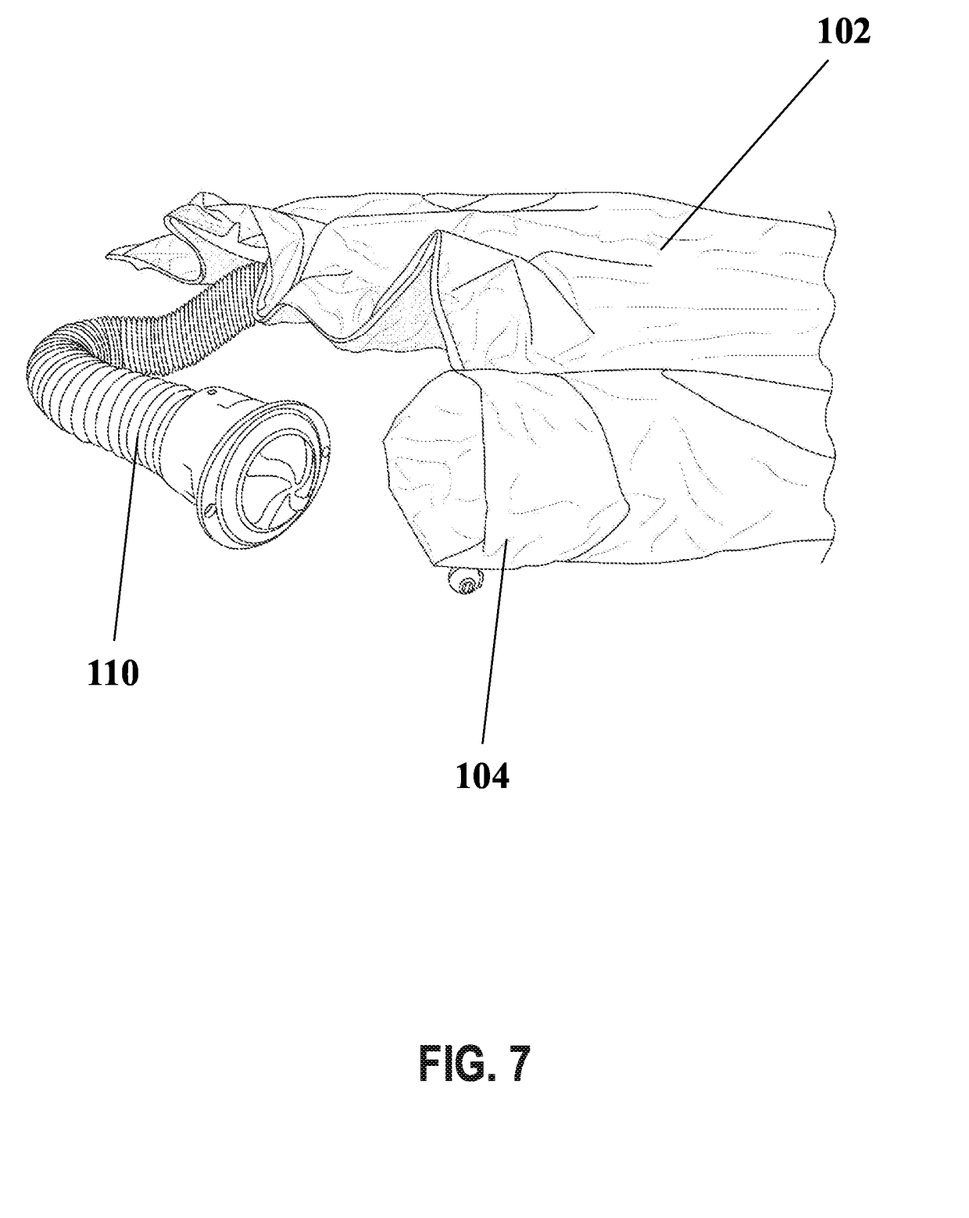
FIG. 7 illustrates a boat's retractable hose or pipe for heating the boat blanket, according to an exemplary embodiment of the present invention.

FIG. 7 illustrates the boat's retractable hose 110 for heating the boat blanket 102, according to an exemplary embodiment of the present invention. One end of the retractable hose 110 may be removably attached to the boat heater hose 108 of the boat and other end of the retractable hose 110 may be inserted into the blanket hose insert 104 of the blanket 102. The retractable hose 110 collects the hot air from the boat heater hose 108 (assuming it is tuned ON and producing the hot air), and circulates it uniformly inside the blanket 102 through the one or more sewn channels 206 via the one or more air channels 402. The blanket 102 prevents the loss of body heat while utilizing the on-board heater hose to keep the surrounding environment of the user warm. The technical specification of the heated boat blanked 102 of the present invention has been shown in the below table.

TABLE 1

| Technical Specification of Heated Boat Blanket | |
|---|---|
| Outer Shell | 70 Denier Ripstop Nylon |
| Water Resistant | Yes |
| Heat Ports | 2 |
| Weight | 3.5 Lbs |
| Drying | Hang Dry Only |
| Inner Fabric | Polar Fleece |
| Wind Proof | Yes |
| Blanket Size | 56" Wide × 68" Long |
| Washing | Machine or Hand |

While the invention has been described in connection with what is presently considered to be the most practical and preferred embodiments, it is to be understood that the invention is not to be limited to the disclosed embodiments, but, on the contrary, is intended to cover various modifications and equivalent arrangements included within the spirit and scope of the appended claims.

What is claimed is:

1. A heated boat blanket, comprising:
   a top layer that is made of nylon and a bottom layer that is made of fleece;
   a plurality of sewn channels formed by sewing the top nylon layer with the bottom fleece layer, wherein the top nylon layer is sewed to the bottom fleece layer such that it includes one or more break points; and
   a plurality of hose inserts, configured for insertion of a retractable hose that is removably attached to a boat heater hose of a boat for collecting hot air, and the hose inserts further configured to circulate the hot air inside the blanket via the plurality of sewn channels;
   wherein the top layer and the bottom layer both comprise a length and a width;
   wherein the plurality of sewn channels are parallel and adjacent to one another and extend at least partially along the length of the blanket;
   wherein each break point is a point where the top and bottom layers are not sewn together;
   wherein the one or more break points are formed between the plurality of sewn channels and extend partially across the width of the blanket in an orthogonal direction with respect to the channels;

wherein the one or more break points are located at a distance at least ½ down the length of the blanket and preferably ¾ down the length of the blanket as measured from a top edge of the blanket.

* * * * *